(12) United States Patent
Montaner et al.

(10) Patent No.: US 11,510,938 B2
(45) Date of Patent: Nov. 29, 2022

(54) USE OF OLIGONUCLEOTIDES FOR THE TREATMENT AND PREVENTION OF PAIN

(71) Applicants: Consejo Nacional de Investigaciones Científicas y Técnicas, Ciudad Autónoma de Buenos Aires (AR); FUNDACION PABLO CASSARA, Ciudad Autónoma de Buenos Aires (AR); UNIVERSIDAD AUSTRAL, Ciudad Autónoma de Buenos Aires (AR)

(72) Inventors: Alejandro Daniel Montaner, Ciudad Autonoma de Buenos Aires (AR); Marcelo Jose Villar, Buenos Aires (AR); Pablo Rodolfo Brumovsky, Buenos Aires (AR); Candelaria Leiguarda, Ramal Pilar (AR); Maria Florencia Coronel, Ciudad Autónoma de Buenos Aires (AR); Inelia Mailín Lara Casadei, Santa Fe (AR); Sandra Sbrascini, Ciudad Autónoma de Buenos Aires (AR)

(73) Assignees: Consejo Nacional de Investigaciones Científicas y Técnicas, Buenos Aires (AR); Fundacion Pablo Cassara, Buenos Aires (AR); Universidad Austral, Buenos Aires (AR)

( * ) Notice: Subject to any disclaimer, the term of this patent is extended or adjusted under 35 U.S.C. 154(b) by 99 days.

(21) Appl. No.: 16/683,677

(22) Filed: Nov. 14, 2019

(65) Prior Publication Data

US 2020/0155592 A1 May 21, 2020

Related U.S. Application Data

(60) Provisional application No. 62/767,549, filed on Nov. 15, 2018.

(51) Int. Cl.
*A61K 31/713* (2006.01)
*A61P 29/02* (2006.01)
*A61K 9/00* (2006.01)

(52) U.S. Cl.
CPC .......... *A61K 31/713* (2013.01); *A61K 9/0019* (2013.01); *A61P 29/02* (2018.01)

(58) Field of Classification Search
CPC .............. C12N 15/117; C12N 2310/17; C12N 2310/315; A61K 31/7115; A61P 25/02
USPC .................... 435/6.1, 91.1, 91.31, 455, 458; 514/44 A, 1; 536/23.1, 24.5
See application file for complete search history.

(56) References Cited

U.S. PATENT DOCUMENTS

| | | | |
|---|---|---|---|
| 2009/0233989 A1* | 9/2009 | Lopez ..................... | A61P 25/00 514/44 R |
| 2021/0040447 A1* | 2/2021 | Zylberberg ............ | A61K 35/17 |

* cited by examiner

*Primary Examiner* — Jane J Zara
(74) *Attorney, Agent, or Firm* — Defillo & Associates, Inc.; Evelyn A. Defillo

(57) ABSTRACT

Method for preventing or treating neuropathic and/or inflammatory pain, wherein said method comprises administering at least one effective dose of the phosphorothioate oligonucleotide IMT504. The preventive method may be applied to a mammal to be subjected to a medical or surgical intervention, or to a mammal that may be injured performing a risky task (for example, a soldier in a battle) to prevent development of pain after a medical intervention or injury.

4 Claims, 12 Drawing Sheets

Specification includes a Sequence Listing.

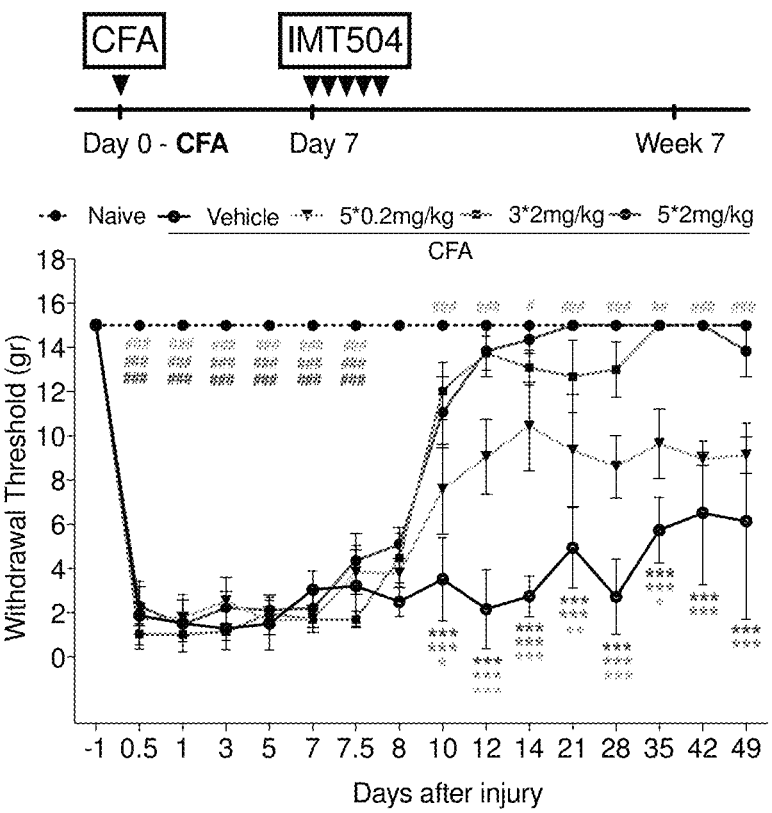
Figure 3A
Figure 3B
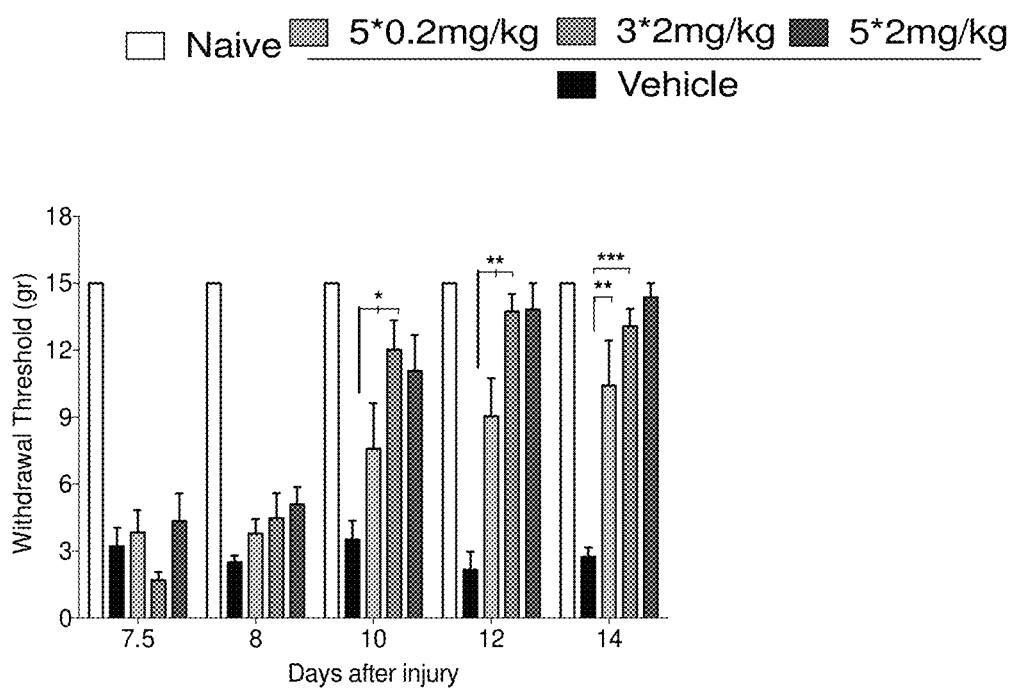
Figure 3C

A

B

SEQUENCE LISTING

```
<160> NUMBER OF SEQ ID NOS: 1

<210> SEQ ID NO 1
<211> LENGTH: 24
<212> TYPE: DNA
<213> ORGANISM: Artificial Sequence
<220> FEATURE:
<223> OTHER INFORMATION: phosphorothioate oligonucleotide IMT504

<400> SEQUENCE: 1
tcatcatttt gtcattttgt catt                                          24
```

USE OF OLIGONUCLEOTIDES FOR THE TREATMENT AND PREVENTION OF PAIN

CROSS REFERENCE TO RELATED APPLICATION

This application claim priority over U.S. Provisional application No. 62/767,549 filed Nov. 15, 2018, the content of which is incorporated herein by reference.

FIELD OF THE INVENTION

The invention refers to a method for preventing pain or for achieving a long-lasting therapeutic effect in a mammal suffering inflammatory and/or neuropathic pain; and uses thereof.

BACKGROUND

Pain is currently classified as nociceptive or neuropathic. Nociceptive pain results from activity in neural pathways secondary to actual tissue damage or potentially tissue-damaging stimuli. In contrast, neuropathic pain is triggered by actual or potential nervous system injuries or dysfunction. Neuropathic pain, as well as certain nociceptive pain conditions (e.g., arthritis), are chronic in nature (Van Hecke O R, et, al., (2014) *Pain* 155(4): 654-62; Gilron I, et al., (2015) *Mayo Clin Proc.*, 90(4): 532-45; Weisman M H, et, al., (2013) *Ann Rheum Dis.*, 72(3): 369-73 and Litwic A, et, al., (2013) *Br Med Bull.*, 105:185-99.

Nociceptive pain results from activation of nociceptors, i.e., the peripheral free nerve-endings of primary afferent neurons (Costigan M, et al., (2009) *Ann Rev Neurosci*, 32: 1-32). The damaged cells and inflammatory leukocytes that are recruited onto the damaged site release cytokines and chemokines that lower the nociceptors' activation threshold. Pain generated during this process is also designated inflammatory pain (Woolf C J. (2010) *J. Clin Invest.*, 120: 3742-3744). After tissue healing, the nociceptors' activation threshold returns to normal levels. Nociceptive pain serves a protecting and physiological purpose; and may be successfully treated by conventional analgesic medication, opioids or anti-inflammatory medicaments. However, certain tissue damage conditions such as arthritis, cause chronic nociceptive pain transmission, often refractory to available treatment options. In contrast, neuropathic pain does not have a physiological role and arises as a consequence of a central and/or peripheral nerve/neuron injury, leading to permanent dysfunctions in the neuronal pathways responsible for pain transmission (Scholz J, et. al., (2002) *Nature Neurosci*, 5: 1062-1067). Neuropathic pain can be caused by various conditions such as diabetes, cancer, infectious diseases, injuries, surgery, or drug toxicity (Baron R, et al., (2010) *Lancet Neurol.*, 9:807-819).

Neuropathic pain cannot be treated with conventional analgesics or anti-inflammatory agents. Currently, there is no drug of choice for the treatment of neuropathic pain. Tricyclic anti-depressants, opioids and anticonvulsants are being used with variable results that, at best, cause an improvement in only a percentage of the patients affected with chronic pain. Moreover, many patients remain refractory to treatment. Finally, most of the drugs specified above also present severe side effects related to their chronic use, this being the main reason for patient non-adherence, despite some therapeutic efficacy.

Altogether, these facts reveal that treatment of neuropathic pain is an unmet clinical need. Consequently, development of innovative drugs in this field is undoubtedly needed.

The synthetic oligodeoxynucleotide designated IMT504 has potent effects on innate and adaptive immune systems of humans, other primates, and rats. Further, IMT504 may increase the number of mesenchymal stem cell (MSC) progenitors, both in vitro and in vivo. Due to its properties, IMT504 has proven to be effective in preclinical assays as a vaccine adjuvant and in the treatment of sepsis and type I diabetes. Surprisingly, it has now been found that pretreatment with IMT504 completely prevents development of experimental inflammatory pain. It was also been unexpectedly found that treatment with IMT504 of a mammal undergoing chronic inflammatory or neuropathic pain suppresses pain for an unusually long period of time as never observed before for any treatment for chronic pain known in the art. Accordingly, treatment with IMT504, as disclosed herein, is an innovative method for preventing chronic pain if the treatment is applied before a surgical intervention that may result in inflammatory and neuropathic pain or for achieving a long-lasting therapeutic effect if applied to a mammal already suffering from chronic inflammation or neuropathic pain.

The synthetic oligodeoxynucleotide designated IMT504 has been used as an immunomodulator (WO/2003/101375), as an osteogenic inducer (EP1807061), as a mesenchymal cell stimulatory agent (WO/2006/128885).

SUMMARY OF THE INVENTION

The present invention provided a method for preventing neuropathic and/or inflammatory pain, wherein the method comprises administering at least one effective dose of the phosphorothioate oligonucleotide IMT504 to a mammal in need thereof and wherein the mammal is a human. The phosphorothioate oligonucleotide IMT504 may comprise SEQ ID No. 1. The neuropathic pain to be prevented may be associated with medical conditions such as trigeminal neuralgia, alcoholism, amputation, cancer, chemotherapy, diabetes, facial nerve problems, atypical facial pain, thyroid problems, multiple myeloma, multiple sclerosis, nerve or spinal cord compression; infectious diseases such as shingles, HIV, syphilis, meningitis, encephalitis, poliomyelitis, epidural abscess; injuries and surgery or drug toxicity; structural defects, such as brain or spinal cord injury, myelopathy, sciatica, Bell's palsy, cervical spondylosis, carpal tunnel syndrome, brain or spinal cord tumors, peripheral neuropathy and Guillain-Barré syndrome, vascular disorders, such as stroke, transient ischemic attack, subarachnoid hemorrhage, subdural hemorrhage and functional disorders, such as headache, epilepsy/seizures, dizziness, neuralgia and hematoma, and extradural hemorrhage, autism, bipolar disorder, catalepsy, depression and neurofibromatosis. Inflammatory pain may result from certain tissue damage conditions, such as for example arthritis; surgical intervention, debilitating conditions such as irritable bowel syndrome and interstitial cystitis; infections, cancer, autoimmune diseases; diseases associated with inflammatory arthritis such as psoriatic arthritis, reactive arthritis and enteropathic arthritis and rheumatoid arthritis; joint inflammatory pain as a consequence of other medical conditions including crystal arthropathies (gout and pseudogout), seronegative spondyloarthropathies including ankylopoietic spondylitis, inflammatory arthritis associated with inflammatory bowel disease, psoriatic arthritis, and reactive arthritis; systemic rheumatologic diseases such as systemic lupus erythematosus, Sjögren's syndrome, mixed collagen tissue disease and dermatomyositis; viral polyarthritis including parvovirus B19, hepatitis, enterovirus, Epstein-Barr and rubella. In a preferred embodiment, at least one dose of between 6 mg/kg and 20 mg/kg is applied over a period of time from 24 hours to 5 days before onset of neuropathic and/or inflammatory pain. In another preferred embodiment, further applied is at least one booster dose of from 2 mg/kg to 6 mg/kg after the onset of neuropathic and/or inflammatory pain, for example at 21 and 30 days from the onset of neuropathic and/or inflammatory pain. Administration may be intravenous, intramuscular, subcutaneous, epidural, or intrathecal.

A method for treating neuropathic and/or inflammatory pain is provided, wherein the method comprises administering at least one effective dose of the phosphorothioate oligonucleotide IMT504 to a mammal in need thereof, wherein the mammal is a human and the phosphorothioate oligonucleotide IMT504 may have SEQ ID No. 1. In a preferred embodiment, the method comprises applying at least one dose of from 0.2 mg/kg to 20 mg/kg, or from 2 to 5 doses over consecutive days. The administration may be intravenous, intramuscular, subcutaneous, epidural, and intrathecal.

Neuropathic pain may comprise medical conditions such as trigeminal neuralgia, alcoholism, amputation, cancer, chemotherapy, diabetes, facial nerve problems, atypical facial pain, thyroid problems, multiple myeloma, multiple sclerosis, nerve or spinal cord compression; infectious diseases such as shingles, HIV, syphilis, meningitis, encephalitis, poliomyelitis, epidural abscess; injuries and surgery or drug toxicity; structural defects, such as brain or spinal cord injury, myelopathy, sciatica, Bell's palsy, cervical spondylosis, carpal tunnel syndrome, brain or spinal cord tumors, peripheral neuropathy and Guillain-Barré syndrome, vascular disorders, such as stroke, transient ischemic attack, subarachnoid hemorrhage, subdural hemorrhage and functional disorders, such as headache, epilepsy/seizures, dizziness, neuralgia and hematoma, and extradural hemorrhage, autism, bipolar disorder, catalepsy, depression and neurofibromatosis. Inflammatory pain may be caused by certain tissue damage conditions, such as for example arthritis; surgical intervention, debilitating conditions such as irritable bowel syndrome and interstitial cystitis; infections, cancer, autoimmune diseases; diseases associated with inflammatory arthritis such as psoriatic arthritis, reactive arthritis and enteropathic arthritis and rheumatoid arthritis; joint inflammatory pain as a consequence of other medical conditions including crystal arthropathies (gout and pseudogout), sero-negative spondyloarthropathies including ankylopoietic spondylitis, inflammatory arthritis associated with inflammatory bowel disease, psoriatic arthritis, and reactive arthritis; systemic rheumatologic diseases such as systemic lupus erythematosus, Sjögren's syndrome, mixed collagen tissue disease and dermatomyositis; viral polyarthritis including parvovirus B19, hepatitis, enterovirus, Epstein-Barr and rubella.

The invention also provides a pharmaceutical composition for preventing or treating neuropathic and/or inflammatory pain, comprising the phosphorothioate oligonucleotide IMT504 and a pharmaceutically acceptable carrier.

BRIEF DESCRIPTION OF THE DRAWINGS

FIG. 1A: Time-line of IMT504 administrations, including concentrations, number of doses and times of administration. Time of hind paw inflammation using Complete Freund's Adjuvant (CFA) is also indicated.

FIGS. 1B, 1C: Administration of IMT504, prior to hind paw inflammation, results in prevention of mechanical allodynia (B) and a certain degree of prevention of cold allodynia (C). Mechanical allodynia only appears 14 days after injury, and is quickly reverted by administration of 3 mg/kg IMT504 on day 28. Mechanical allodynia returns by day 35 (B). Rats receiving IMT504, both at day 28 or day 3 before injury, exhibit a very slow increase in cold withdrawal frequency, reaching moderate to high levels 21 days after injury. Rats receiving IMT504 only three days before injury exhibit a more moderate anti-allodynic effect, although a reinforcement dose 28 days after injury using 50% of the effective dose of IMT504 results in full anti-allodynic effect that is lost 35 days after injury (C). Asterisks compare groups. Numerals compare 21 days versus previous days in the IMT504 28- and 3d-treated rats.

FIGS. 1D, 1E: Administration of IMT504, prior to hind paw inflammation, does not prevent occurrence of inflammation, which remains high throughout the whole tested period. Dotted line in (B) shows the level of inflammation observed in injured rats receiving no treatment. Analysis of dermal and epidermal thickness, comparing contralateral and ipsilateral hind paws, 35 days after injury, show a marked increase in thickness. Such an effect is most evident in the dermis, and is only lightly significant in the epidermis (C). Asterisks compare contralateral vs. ipsilateral.

FIG. 2A: Time-line of CFA-induced hind paw inflammation, Early Treatment (ET) and Late Treatment (LT) protocols initiation and behavioral tests ending.

FIG. 2B: While naïve rats (n=3) virtually always exhibited basal withdrawal thresholds, all injured animal groups showed ipsilateral mechanical allodynia one day after intraplantar CFA. Untreated CFA rats (n=5) remained allodynic throughout the tested time period. Rats on ET protocol (n=5) exhibited progressive recovery, reaching basal levels seven days after treatment initiation. Rats in the LT protocol (n=5) remained allodynic during the first week after injury, and then begun recovery towards basal levels, fully achieved seven days after initiation of the treatment. Both ET and LT groups maintained basal withdrawal thresholds once IMT504 treatment took effect.

FIG. 2C: Naïve rats treated with a daily dose of 20 mg/kg IMT504 for five consecutive days and observed for up to 22 days, did not shown changes in mechanical withdrawal thresholds (upper panel) or tail withdrawal latencies (lower panel). Statistically significant differences are shown between naïve and IMT504-treated rats (#) and CFA injured rats untreated and IMT504-treated (*).

FIGS. 3A-3C show the effects of late treatment using different low doses of IMT504 on pain-like behavior in rats with hind paw inflammation.

FIG. 3A: Time-line of CFA-induced hind paw inflammation, LT protocol initiation and behavioral tests ending.

FIG. 3B: While naïve rats (n=5) virtually always exhibited basal withdrawal thresholds, all injured animal showed ipsilateral mechanical allodynia already 12 hours (h) after intraplantar CFA. Vehicle-treated CFA rats (n=9) remained allodynic throughout the whole testing period. Rats in the LT protocol receiving three doses (n=5) or five early doses (n=5) of 2 mg/kg of IMT504 remained allodynic only during the first week after injury, beginning recovery three days after initiation of the treatment, reaching basal ipsilateral withdrawal thresholds at day five after initiation of the treatment and onwards. Rats receiving 5 daily doses of 0.2 mg/kg of IMT504 (n=5) showed a slower, incomplete recovery, never reaching basal withdrawal thresholds. Rats receiving three or five daily doses of 2 mg/kg of IMT504 maintained basal withdrawal thresholds throughout the whole assay period.

FIG. 3C: Comparison between treatment protocols showed significant differences 10 to 14 days, and four to seven weeks after injury, between rats receiving a daily dose of 2 mg/kg IMT504 for three or five consecutive days and those receiving a daily dose of 0.2 mg/kg of IMT504 for five consecutive days. In B, statistically significant differences are shown between naïve and IMT504 treated rats (#) and untreated and IMT504-treated CFA injured rats (*). In C, statistically significant differences are shown between IMT504-treated groups (*).

FIG. 5A shows a graph showing the evolution of cold allodynia, expressed as frequency of withdrawal, before and after (arrow) IMT504 administration. Statistical analysis shows differences between contralateral hind paw withdrawal thresholds (unified in one single curve due to lack of differences between groups) and ipsilateral thresholds using numeral markers (#; black, contralateral vs. untreated SNI; red, contralateral vs. ipsilateral IMT504-treated). Asterisks (*) show differences between ipsilateral hind paw withdrawal thresholds in SNI-untreated rats and the ipsilateral withdrawal thresholds in rats receiving IMT504.

FIG. 5B shows a graph showing the evolution of cold allodynia, expressed as cold score, before and after (arrow) IMT504 administration. Statistical analysis shows differences between contralateral hind paw withdrawal thresholds (unified in one single curve due to lack of differences between groups) and ipsilateral thresholds using numeral markers (#; black, contralateral vs. untreated SNI; red, contralateral vs. ipsilateral IMT504-treated). Asterisks (*) show differences between ipsilateral hind paw withdrawal thresholds in SNI-untreated rats and the ipsilateral withdrawal thresholds in rats receiving IMT504.

DETAILED DESCRIPTION OF THE INVENTION

Definitions

Figure 1:
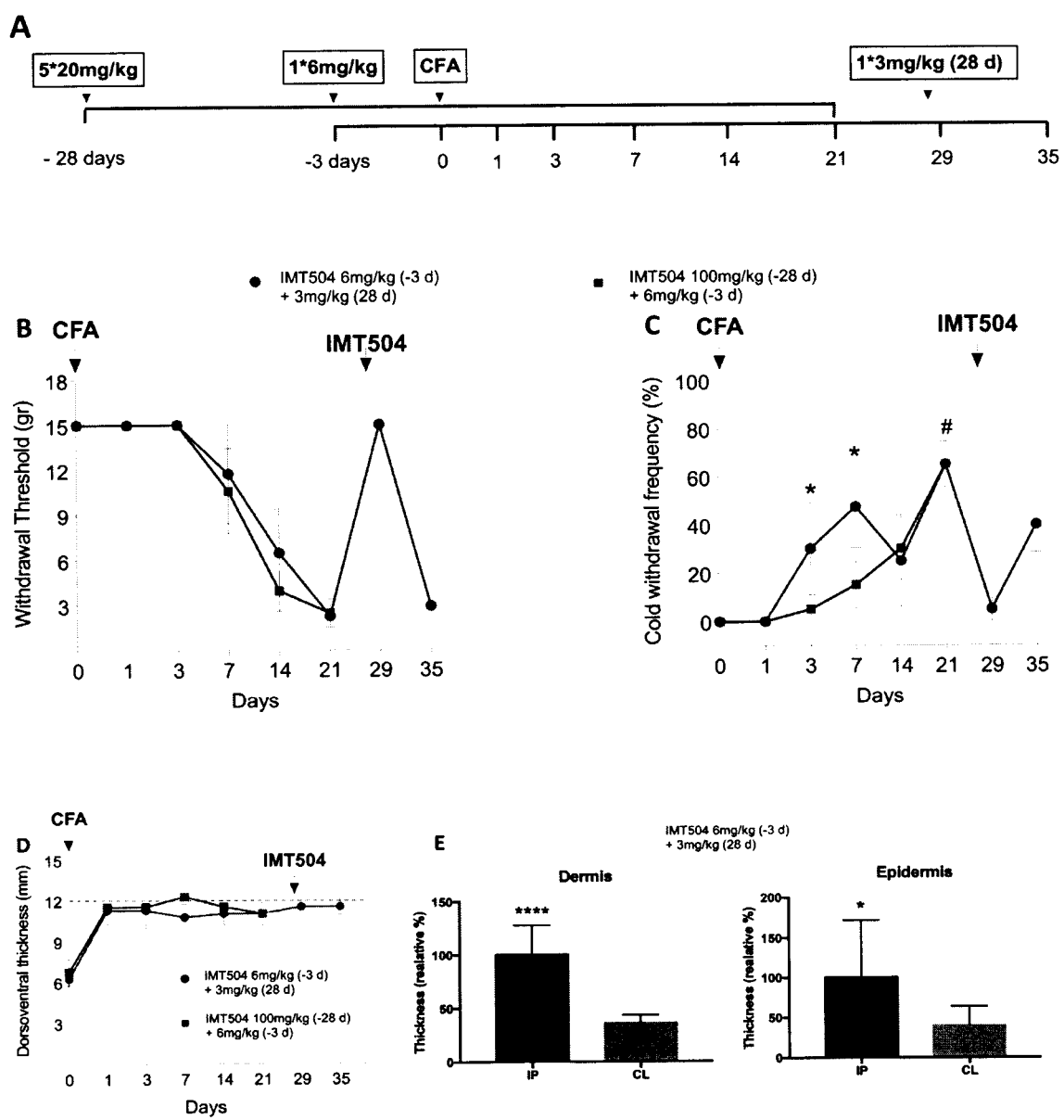
FIGS. 1A-1E show the effects of preventive treatment with IMT504 and an additional booster using 50% of an effective dose on mechanical and thermal allodynia. Effects on hind paw edema and dermal and epidermal thickness.

The terms preventive and pre-emptive are used interchangeably and refer to a previous treatment intended to reduce the pain that an individual will suffer at a later time.

The acronym ET means preventive or early treatment.

The acronym LT refers to a late treatment to be performed after occurrence of pain symptoms.

The method comprises administering a parenteral dosage form containing the oligonucleotide with phosphorothioate bonds, IMT504, for example, but not limited to, the oligonucleotide having the sequence (SEQ ID No. 1) TCATCATTGTCATTTTGTCATT, to a mammal that will be subjected to a medical intervention (e.g. surgical intervention) or that may be injured due to a risky task (e.g. a soldier in a battle) to avoid development of pain after the medical intervention or injury. The method also comprises administering a parenteral dosage form containing the phosphorothioate oligonucleotide IMT504 having the sequence of SEQ ID No. 1, to a mammal suffering ongoing pain to achieve a long-lasting therapeutic effect.

The method may be used for different central nervous system (consists of the brain and spinal cord) and peripheral nervous system (consists of all other neural elements, including the peripheral nerves and the autonomic nerves) disorders, associated with neuropathic or inflammatory pain, such as: infections, meningitis, encephalitis, poliomyelitis, epidural abscess, and shingles.

In another embodiment, the method may be used for degeneration and autoimmune disorders, such as Parkinson disease, multiple sclerosis, amyotrophic lateral sclerosis (ALS), motor neuron disease (MND), Huntington chorea, and Alzheimer disease.

In another embodiment the method may be used for structural defects, such as brain or spinal cord injury, myelopathy, sciatica, Bell's palsy, cervical spondylosis, carpal tunnel syndrome, brain or spinal cord tumors, peripheral neuropathy and Guillain-Barré syndrome, vascular disorders, such as stroke, transient ischemic attack (AIT), subarachnoid hemorrhage, subdural hemorrhage and functional disorders, such as headache, epilepsy/seizures, dizziness, neuralgia and hematoma, and extradural hemorrhage, autism, bipolar disorder, catalepsy, depression and neurofibromatosis.

The invention provides a method for preventing neuropathic and/or inflammatory pain or achieving a long-lasting therapeutic effect in a mammal suffering neuropathic and/or inflammatory pain. The method comprises administering a parenteral dosage form containing the phosphorothioate oligonucleotide IMT504, to a mammal that will be subjected to a medical intervention or that will perform a risky task that may result in inflammation and potential nerve injury, in order to avoid development of acute and/or chronic pain. A typical example are surgical interventions, undergoing both of acute pain during the first week after the intervention, as well as the potential development of chronic neuropathic pain over time, a condition affecting up to 60% of operated patients. In addition to this example, this method may be employed in other relevant situations, such as pain and injuries induced by trauma resulting from military tasks in combat or injury produced as a result of any other risky task. Finally, debilitating conditions such as irritable bowel syndrome and interstitial cystitis, typically associated to chronic inflammation, are also within the scope of the invention. In a preferred embodiment, the method is used for preventing pain.

Some examples of medical conditions associated with neuropathic pain are: trigeminal neuralgia, alcoholism, amputation, cancer, chemotherapy, diabetes, facial nerve problems, HIV infection, multiple myeloma, multiple sclerosis, nerve or spinal cord compression, shingles, syphilis, atypical facial pain and thyroid problems. Many other medical conditions are also associated with neuropathic pain, such as a number of rare genetic disorders, and are within the scope of the invention.

Some embodiments of the invention include a dosage form comprising IMT504 in an isotonic buffer (e.g. buffered saline) adequate for parenteral use. Other embodiments of the invention include a method for preventing neuropathic pain comprising administering a parenteral dosage form containing IMT504 to a mammal before a medical intervention (e.g. surgical intervention or to a person that will perform a task that may likely result in an injury (e.g. military task in combat), in order to suppress or alleviate post-intervention or post-trauma-derived acute and/or chronic pain. In this case, the dosage form should be administered between 24-72 hours before the medical intervention.

Another embodiment of the invention includes a method for long-lasting suppression or relieving of pain comprising administration of a parenteral dosage form containing IMT504 to a mammal suffering chronic inflammatory and/or neuropathic pain.

Another embodiment of the invention includes a pharmaceutical product comprising one or more units of a parenteral dosage form described herein, wherein each unit contains from 0.1 mg to 100 mg of IMT504. Preferably the dosage unit contains between 10 to 50 mg of IMT504. The treatment may consist of as many parenteral doses as needed injected on consecutive days or every other day as needed. Preferably, the treatment consists of five doses injected on successive days. Preferred parenteral routes are intramuscular (i.m.) or subcutaneous (s.c.).

Preventive Treatment with IMT504 in Rats with Chronic Inflammation:

An assay was conducted to address the preventive effect of IMT504 in rats with chronic inflammation, as described in Example 2. Briefly, two groups of four rats each were used. One group received a daily dose of 20 mg/kg IMT504 for five consecutive days and four weeks later received one additional dose of 6 mg/kg of IMT504. The second group only received the dose of 6 mg/kg of IMT504, and an additional single administration of 3 mg/kg of IMT504, 28 days after injury. Both groups received intra-plantar CFA, three days after the single dose of 6 mg/kg and their mechanical and thermal withdrawal thresholds were tested 1, 3, 7, 14, 21, 29, and 35 days after injury (FIG. 1A).

In both groups, rats exhibited lack of mechanical allodynia during the first three days after CFA-induced inflammation. Mechanical withdrawal thresholds began a progressive decrease by day 7 after injury and onwards, reaching allodynic levels 14 days after injury. Twenty-one days after injury, all animals reached basal allodynic levels (FIG. 1B), comparable to untreated CFA-rats (see FIG. 2).

Concerning responses to cold stimulation, rats receiving a daily dose of 20 mg/kg IMT504 for five consecutive days plus a single dose of 6 mg/kg IMT504 three days before CFA injection, exhibited a slow progression towards cold allodynia (reaching a peak 21 days after injury). Rats only receiving a single dose of 6 mg showed milder protection against cold allodynia, and also reaching a peak of cold allodynia 21 days after injury. Interestingly, both groups, even twenty days after injury, only showed 60% frequency of cold allodynia (FIG. 1C); this is in contrast to rats with CFA-inflammation but no treatment, where allodynia began one day after injury and was maintained throughout several days.

An additional administration of 3 mg/kg of IMT504, 28 days after injury, resulted in complete reduction in mechanical and cold allodynia, as observed one day after re-administration (FIG. 1C). Thirty-five days after injury, rats returned to basal mechanical allodynia and a certain degree of cold allodynia (FIG. 1C).

Finally, both groups of rats showed consistently elevated hind paw dorsoventral thicknesses throughout the entire tested period, starting one day after injury (FIG. 1D), mostly at the expense of an increase in the thickness of the dermis (FIG. 1E). Preventive IMT504-treatment did not seem to alter the natural course of hind paw inflammation.

IMT504 parenteral treatment provides long-lasting therapeutic effect in models of inflammatory and neuropathic pain.

Effects of a Daily Dose of 20 mg/kg IMT504 for Five Consecutive Days in ET and LT Protocols on Mechanical Withdrawal Threshold.

An assay was conducted to address the effect of IMT504 at a concentration of 20 mg/kg (a daily injection for five consecutive days) on hind paw mechanical withdrawal thresholds.

All CFA rats, regardless of their treatment, exhibited a clear reduction in ipsilateral mechanical withdrawal thresholds, reaching allodynic levels, as early as one day after injury (FIG. 2B). Untreated CFA rats remained allodynic throughout the entire tested period.

In contrast, CFA rats on the ET protocol exhibited a progressive increasing in withdrawal thresholds, starting on the third day after initiation of the treatment, reaching basal thresholds seven days after injury and onwards. On the other hand, CFA rats on the LT protocol showed recovery of basal mechanical withdrawal thresholds starting one week after treatment (two weeks after injury), and remaining normal from there on. Thus, significant differences were observed between untreated and IMT504-treated CFA animals, starting seven days after administration of the ODN (p<0.001) (FIG. 2B).

Finally, in naïve rats (FIG. 2B) and in the contralateral hind paws (data not shown) of IMT504-treated or untreated-CFA rats, withdrawal thresholds remained normal during this assay.

Effects of a Daily Dose of 20 mg/kg of IMT504 for Five Consecutive Days in Naïve Rats on Hind Paw Mechanical Withdrawal Threshold and Tail Heat Nociception:

Naïve rats receiving a daily dose of 20 mg/kg IMT504 for five consecutive days did not show any evident changes in hind paw mechanical withdrawal or tail thermal withdrawal latencies, remaining always comparable to saline-treated naïve rats (FIG. 2C).

Effects of Different Concentrations of IMT504 on Mechanical Withdrawal Threshold in LT Protocols Using a Daily Injection for Three or Five Consecutive Days:

Assays focused on the LT protocol were carried out, exploring different IMT504 doses and number of injections on mechanical withdrawal thresholds in CFA rats. As observed during the test, all animals undergoing plantar CFA injection exhibited a dramatic decrease in withdrawal thresholds, showing mechanical allodynia already twelve hours after injury (FIG. 3B). Vehicle-treated CFA rats maintained the same degree of allodynic behavior throughout the entire assay, in contrast with IMT504-treated or naïve rats (p<0.001) (FIG. 3B).

On the other hand, CFA rats on LT protocols exhibited a progressive recovery towards basal mechanical withdrawal thresholds starting at day 10 after injury (p<0.001); the effect seemed to be dose-dependent. Thus, rats treated with three early doses or five early doses of 2 mg/kg IMT504 showed a faster recovery of basal withdrawal thresholds, reaching basal levels between 10 and 12 days after injury and maintaining such a condition throughout the entire assay (seven weeks). On the other hand, CFA rats a daily dose of 0.2 mg/kg IMT504 for five consecutive days also showed an increase in mechanical withdrawal threshold, albeit not reaching the basal level. Moreover, these rats showed no significant differences with the vehicle-treated CFA rats (p>0.05) towards the end of the assay (FIG. 3B).

Comparisons between treatments showed differences between groups receiving a daily dose of 0.2 mg/kg of IMT504 for five consecutive days, and a daily dose of 2 mg/kg of IMT504 for three or five consecutive days, starting 10 days after injury and persisting throughout the assay (p<0.05) (FIG. 3C).

Finally, and as observed during a previous assay, in naïve rats (FIG. 3B, C), and in the contralateral hind paws of IMT504-treated or vehicle-treated CFA rats, the withdrawal thresholds exhibited normal basal values (data not shown).

Figure 4:
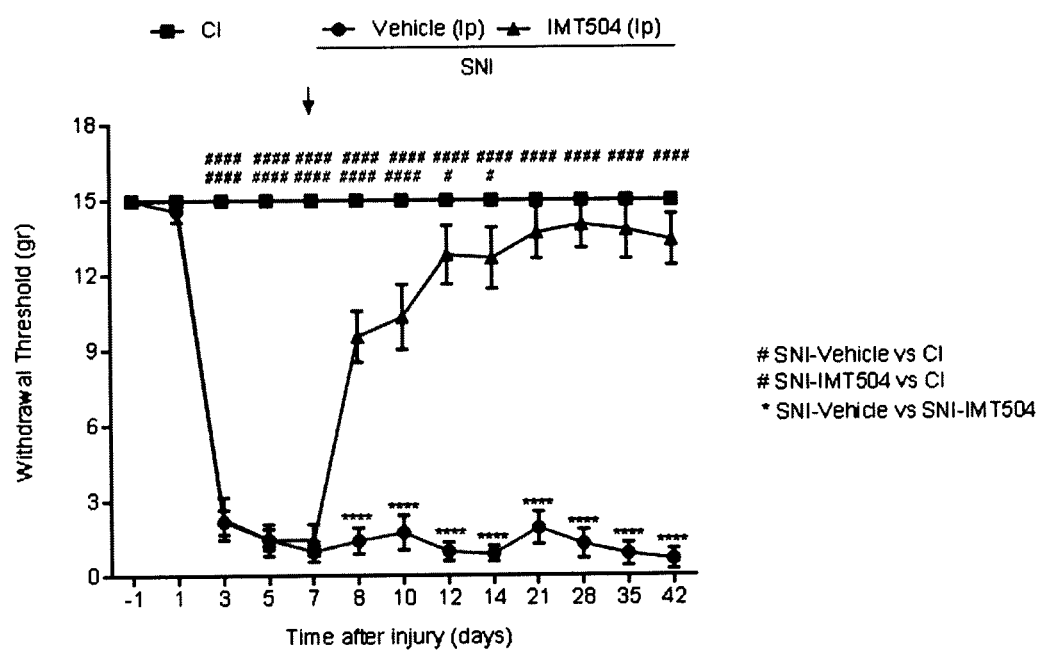
FIG. 4 shows the effects of single dose 6 mg/kg IMT504 treatment on mechanical thresholds in a model of rats with spared nerve injury (SNI): Graph showing the evolution of mechanical allodynia before and after (arrow) IMT504 administration. Statistical analysis shows differences between contralateral hind paw withdrawal thresholds (unified in one single curve due to lack of differences between groups) and ipsilateral thresholds using numeral markers (#; black, contralateral vs. untreated SNI; red, contralateral vs. ipsilateral IMT504-treated). Asterisks (*) show differences between ipsilateral hind paw withdrawal thresholds in SNI-untreated rats and the ipsilateral withdrawal thresholds in rats receiving IMT504.
Figure 5A:
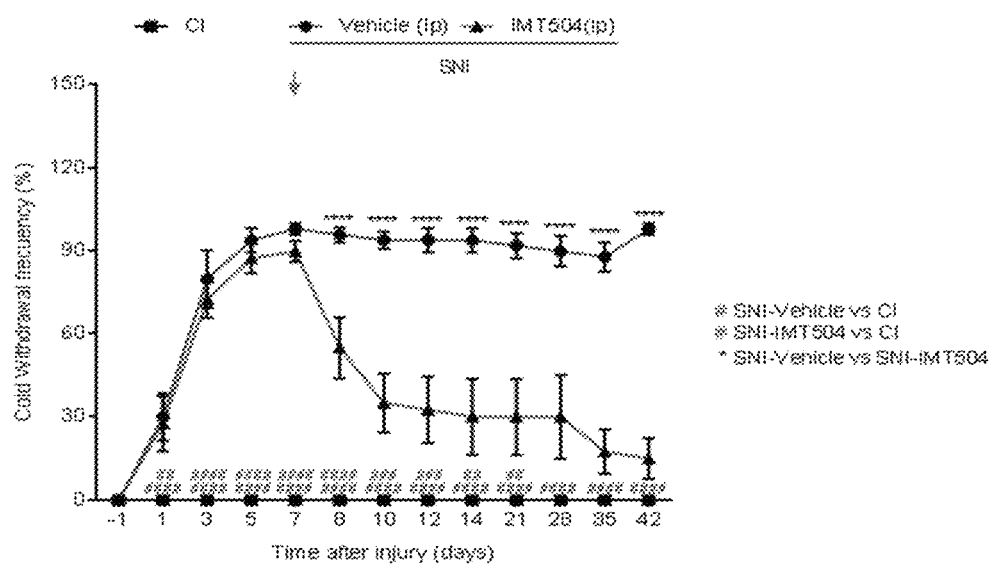
FIGS. 5A-5B show the effects of single dose 6 mg/kg MT504 treatment on cold allodynia in rats with SNI.

Effects of a Single Dose of 6 mg/kg IMT504 in a LT Protocol, on Mechanical and Thermal Withdrawal Thresholds in Rats with SNI:

All animals subjected to SNI developed quick and long-lasting mechanical (FIG. 4) and cold allodynia (FIGS. 5A, B). Rats receiving a dose of 6 mg/kg of IMT504 seven days after injury showed a progressive and rapid increase in mechanical withdrawal thresholds (mechanical allodynia reduction), almost at basal levels starting 12 days after injury, to become fully recovered from week three and onwards (FIG. 4).

Figure 5B:
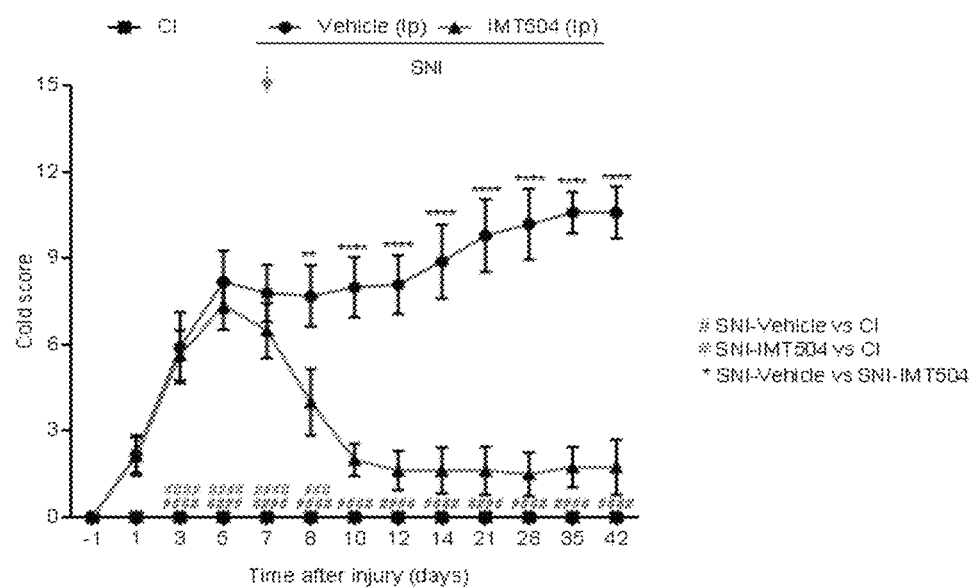

In the same manner, recovery from cold allodynia, as measured by the frequency of paw withdrawal (FIG. 5A), as well as by the scoring of pain-like behavior due to cold stimulation (FIG. 5B), was observed. While cold withdrawal frequency took longer to be reduced to basal levels (three weeks after injury; FIG. 5A), cold scores were reduced to basal levels ten days after injury and onwards (FIG. 5B).

Figure 6:
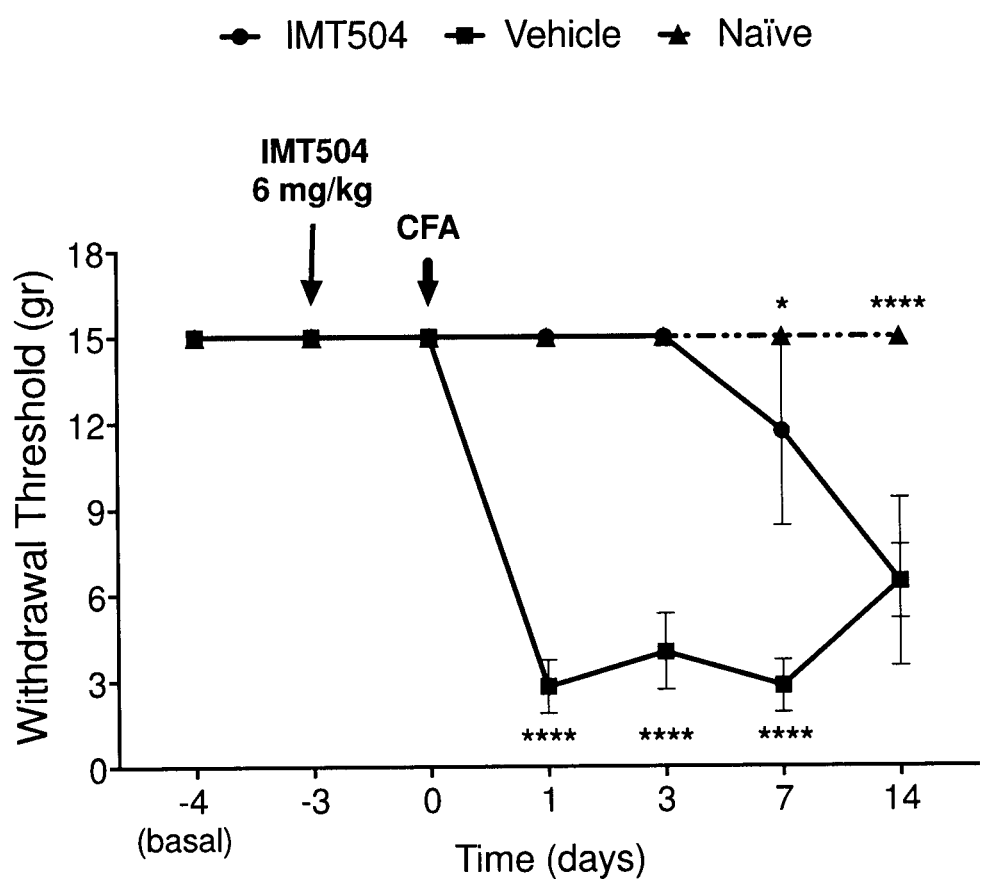
FIG. 6 shows the effects of a pre-emptive treatment with IMT504 on mechanical allodynia in rats with plantar inflammation: Graph showing evolution of mechanical allodynia when 6 mg/kg of IMT504 administration is carried out three days before inflammation with CFA (arrow). Black asterisks (*) show differences between ipsilateral hind paw withdrawal thresholds in rats treated with IMT504 vs. naïve rats. Red asterisks (*) show differences between ipsilateral hind paw withdrawal thresholds in rats treated with IMT504 vs. rats treated with vehicle.

FIG. 6 shows the effect of preventive treatment with IMT504 on mechanical allodynia in rats with hind paw inflammation. Rats receiving vehicle (n=4) 3 days before hind paw inflammation show a rapid decrease in mechanical withdrawal thresholds after injury, becoming allodynic already 1 day after inflammation, and maintaining such a state for at least 14 days. In contrast, in rats receiving IMT504 (n=4), 3 days previous to hind paw inflammation, occurrence of mechanical allodynia is considerably delayed. In these rats, IMT504 prevents mechanical allodynia during the first 7 days after the induction of hind paw inflammation, at which point the withdrawal thresholds begins to decrease, reaching allodynic levels comparable to vehicle-treated rats 14 days after injury. Asterisks show statistically significant differences when comparing the withdrawal thresholds of IMT504-treated rats vs. naïve (black asterisks) or vehicle-treated rats (red asterisks).

Figure 7:
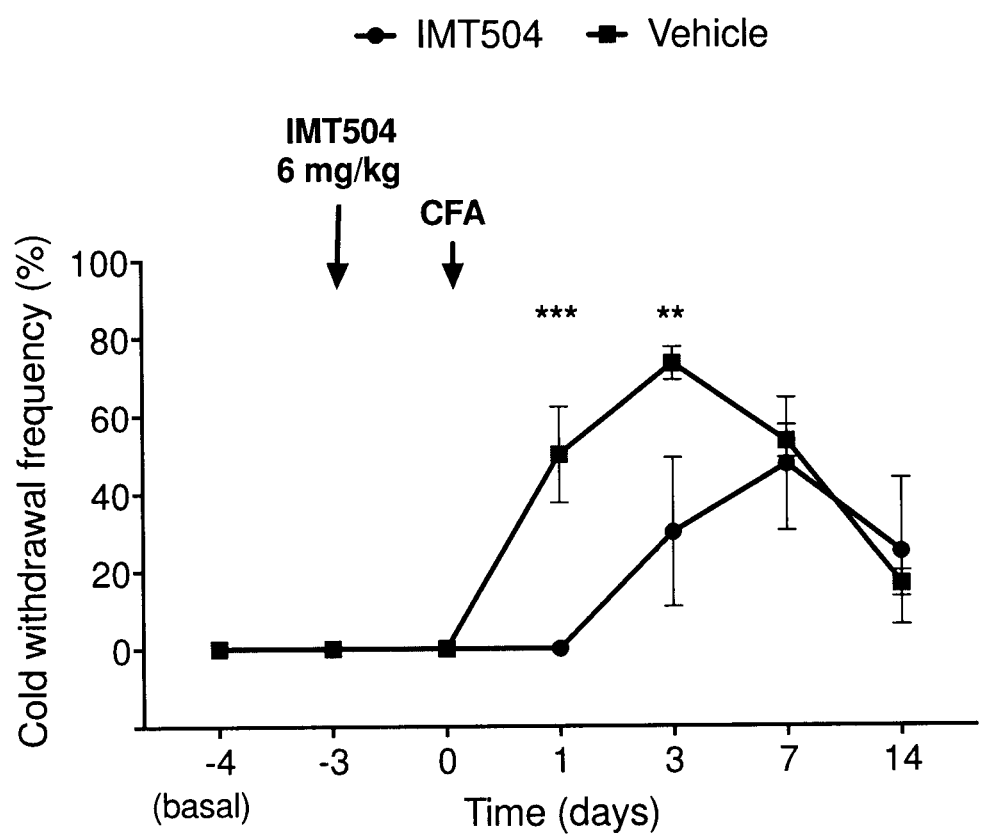
FIG. 7 shows the effects of pre-emptive treatment with IMT504 on thermal allodynia in rats with plantar inflammation: Graph showing evolution of thermal allodynia when 6 mg/kg of IMT504 administration is carried out three days before inflammation with CFA (arrow). Asterisks (*), show differences between rats treated with IMT504 vs. rats treated with vehicle.

FIG. 7 shows effects of preventive treatment with IMT504 on cold allodynia in rats with hind paw inflammation. Rats receiving vehicle (n=4) 3 days before hind paw inflammation show a rapid increase in cold withdrawal frequency after injury, becoming allodynic already 1 day after inflammation, and maintaining such a state for at least 3 days, before returning towards basal withdrawal to cold stimuli (0%). In contrast, in rats receiving IMT504 (n=4), 3 days previous to hind paw inflammation, results in delayed cold allodynia. In these rats, IMT504 prevents cold allodynia during the first 1 day after the induction of hind paw inflammation, at which point the withdrawal frequency begins a slow increase, reaching allodynic levels comparable to vehicle-treated rats 7 days after injury, a time at which both vehicle- and IMT504-treated rats show a clear tendency towards basal responses to cold stimulation. Asterisks show statistically significant differences when comparing the withdrawal thresholds of vehicle- or IMT504-treated rats.

Figure 8:
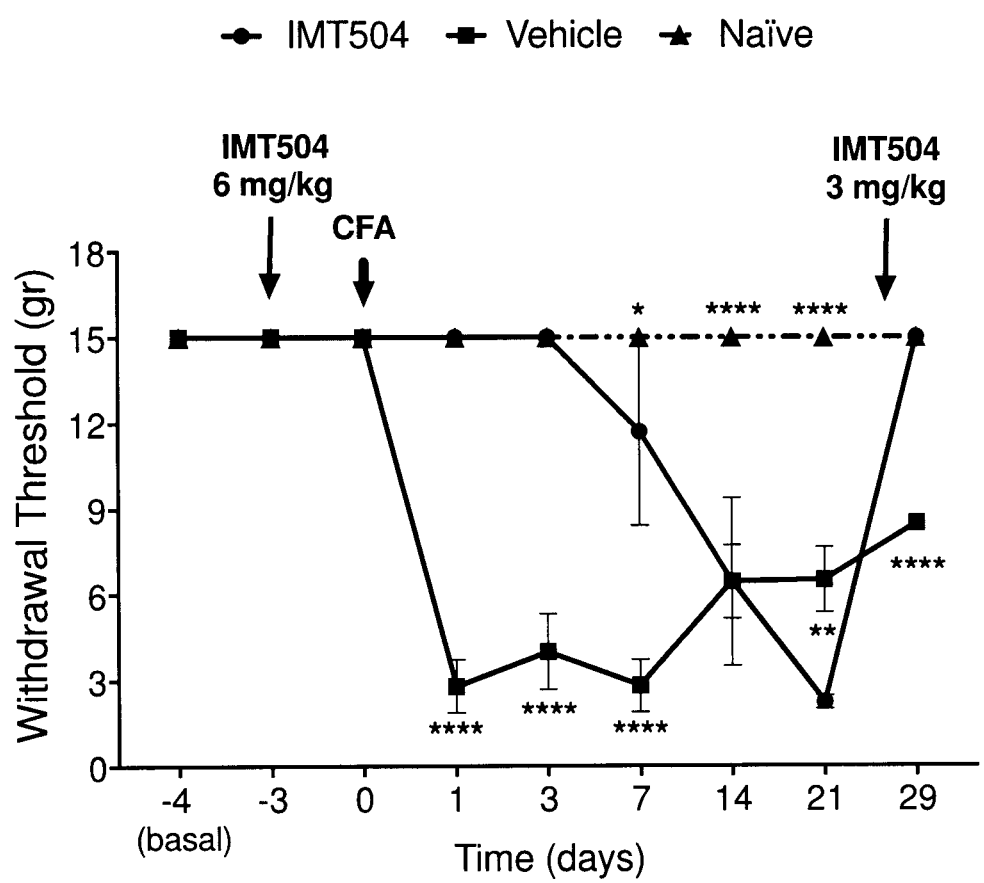
FIG. 8 shows the effects of pre-emptive treatment with IMT504 (6 mg/kg) on mechanical allodynia in rats with plantar inflammation, with a booster dose (3 mg/kg) by day 28: Asterisks (*) show differences between ipsilateral hind paw withdrawal thresholds in rats treated with IMT504 vs. rats treated with vehicle.

FIG. 8 shows the effects of preventive treatment with IMT504 on mechanical allodynia in rats with hind paw inflammation, with a half-dose reinforcement at day 28: Rats receiving vehicle (n=4) 3 days before hind paw inflammation show a rapid decrease in mechanical withdrawal thresholds after injury, becoming allodynic already 1 day after inflammation, and maintaining such a state for at least 29 days. In contrast, in rats receiving IMT504 (n=4), 3 days previous to hind paw inflammation, considerably delays the occurrence of mechanical allodynia. In these rats, IMT504 prevents mechanical allodynia during the first 7 days after the induction of hind paw inflammation, at which point the withdrawal thresholds begins to decrease, reaching allodynic levels comparable to vehicle-treated rats 14 days after injury. A new administration of IMT504, 28 days after injury and at 50% de effective dose (3 mg/kg), results in full recovery of basal withdrawal thresholds. Asterisks show statistically significant differences when comparing the withdrawal thresholds of IMT504-treated rats vs. naïve (black asterisks) or vehicle-treated rats (red asterisks).

Figure 9:
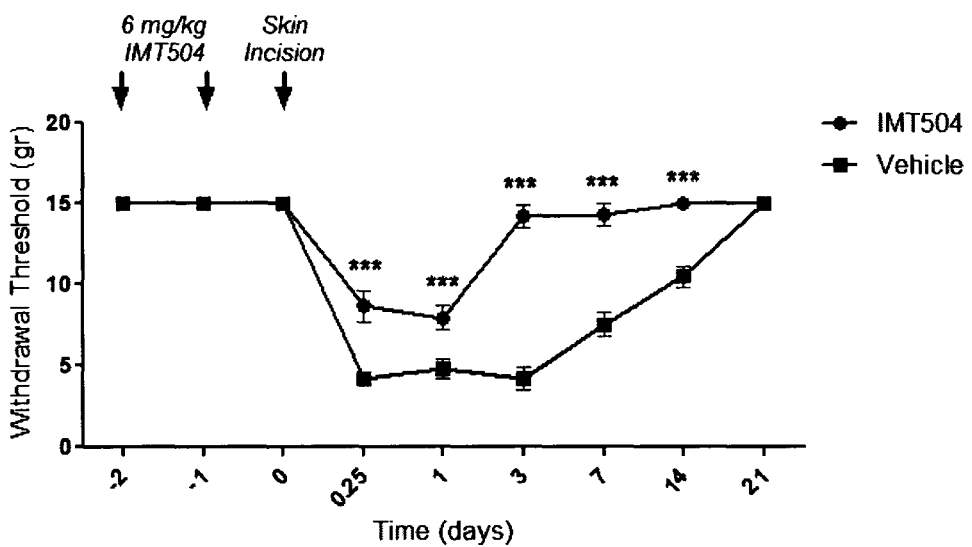
FIGS. 9A and 9B show the effects of pre-emptive treatment with IMT504 (6 mg/kg; 48 h and 24 h before injury) on mechanical and thermal allodynia in rats subjected to plantar incision: Asterisks (*) show significant differences between ipsilateral withdrawal thresholds (A) in rats treated with IMT504 vs. rats treated with vehicle.
Figure 9:
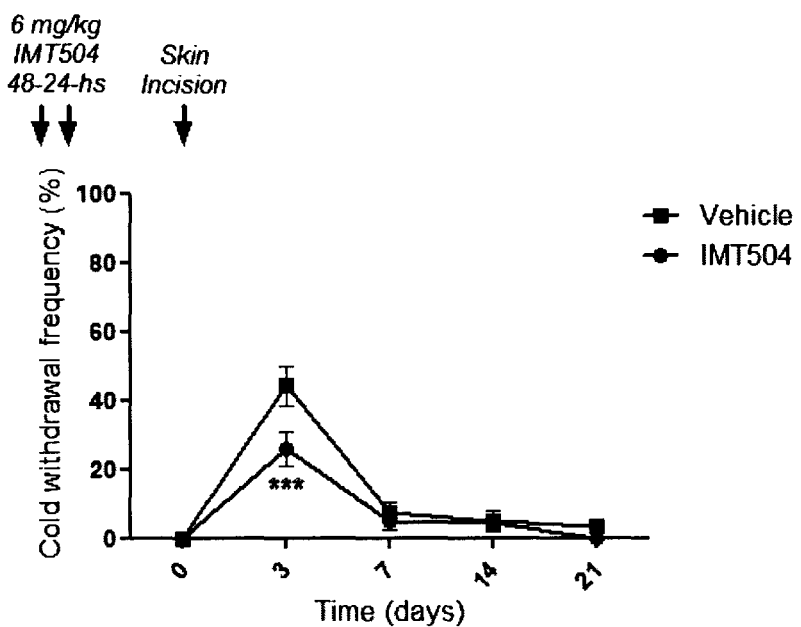

Effects of Two Preventive Doses of IMT504 (6 mg/kg; 48 and 24 hs Before Injury) on Mechanical Withdrawal Threshold and Cold Allodynia, in Rats with Post-Incisional Pain:

An assay was conducted to address the effect of IMT504 at a concentration of 6 mg/kg (two injections, one at 48 h and a second at 24 h before injury) on hind paw mechanical withdrawal thresholds. All rats subjected to an incision of hind paw skin and that received vehicle 48 and 24 h before injury showed a clear reduction in ipsilateral mechanical withdrawal thresholds, reaching allodynic levels as soon as 6 h after injury (FIG. 9A). These rats maintained mechanical allodynia during at least 3 days after injury, after which they started to show a slow recovery of basal withdrawal thresholds, and full recovery thereof at 21 days after injury (FIG. 9A). In contrast, rats subjected to a unilateral incision of hind paw skin and that received preventive IMT504 showed a lower reduction of withdrawal thresholds at 6 h and 1 day after injury as compared to rats receiving vehicle. From day 3 and on, rats previously treated with IMT504 showed basal withdrawal thresholds (FIG. 3A). Significant differences were observed between vehicle-treated rats and IMT504-treated rats, 6 h and 1, 3, 7, 14 and 21 days after injury (p<0.001) (FIG. 9A).

An analysis of cold allodynia showed that rats with post-incisional pain receiving preventive vehicle developed a transient cold allodynia, with one peak 3 days after injury (FIG. 9B). In contrast, rats with post-incisional pain receiving preventive IMT504 showed a significant reduction in cold allodynia, particularly apparent 3 days after injury (FIG. 9B).

Finally, both mechanical withdrawal thresholds as well as responses to cold stimuli in contralateral hind paws of rats treated with IMT504 or treated with vehicle remained normal during these assays (data not shown).

Parenteral preventive treatment with IMT504 transiently prevents chronic inflammatory pain without altering the inflammatory state of the affected hind paw.

Figure 10:
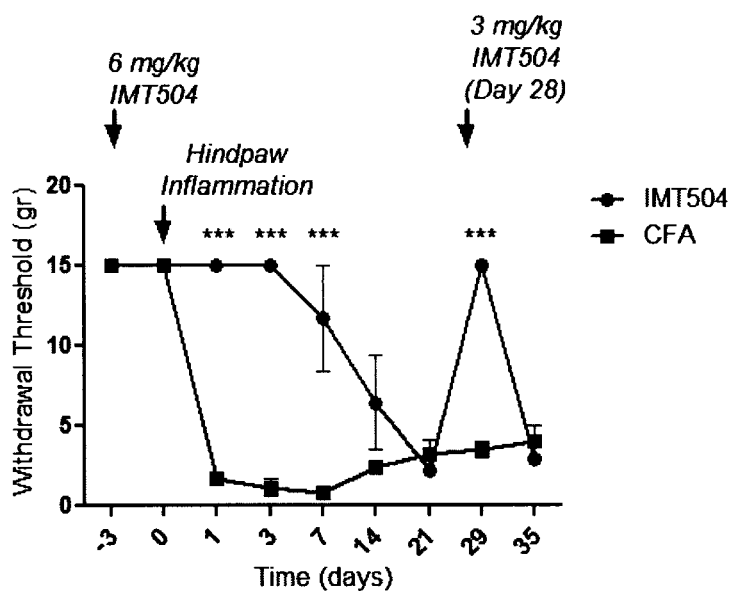
FIGS. 10A-10B show the effects of pre-emptive treatment with IMT504 (6 mg/kg; 72 h before injury) and a booster dose (3 mg/kg) by day 28, on mechanical allodynia and thickness of paw in rats subjected to plantar inflammation: (A) Asterisks (*) show significant differences between ipsilateral hind paw withdrawal thresholds in rats treated with IMT504 vs. rats treated with vehicle. (B) Asterisks (*) show significant differences between thickness of ipsilateral paws of rats treated with IMT504 vs. untreated rats (CFA) vs. naïve rats. Numerals show significant differences in thicknesses of ipsilateral paws of rats treated with IMT504 vs. untreated rats (CFA). A withdrawal threshold of less than 6 is considered allodynia.
Figure 10:
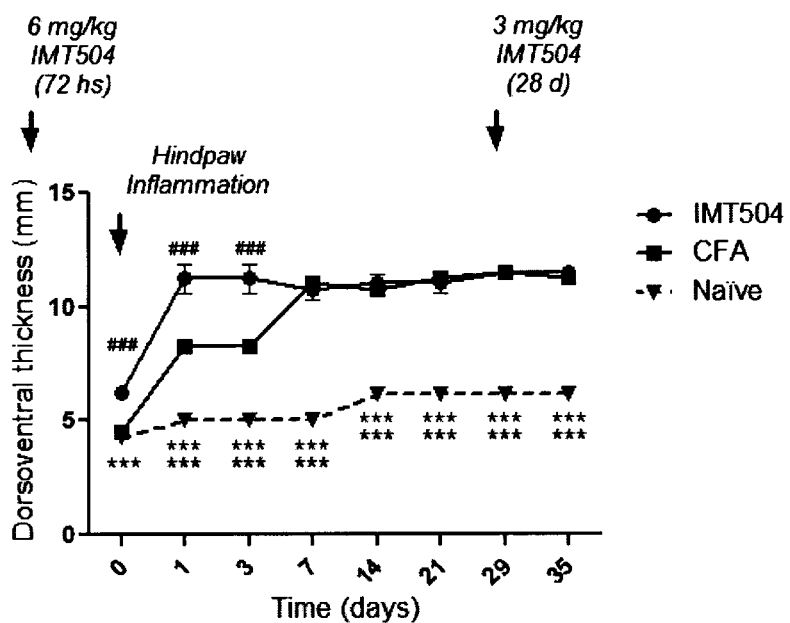
Figure 11:
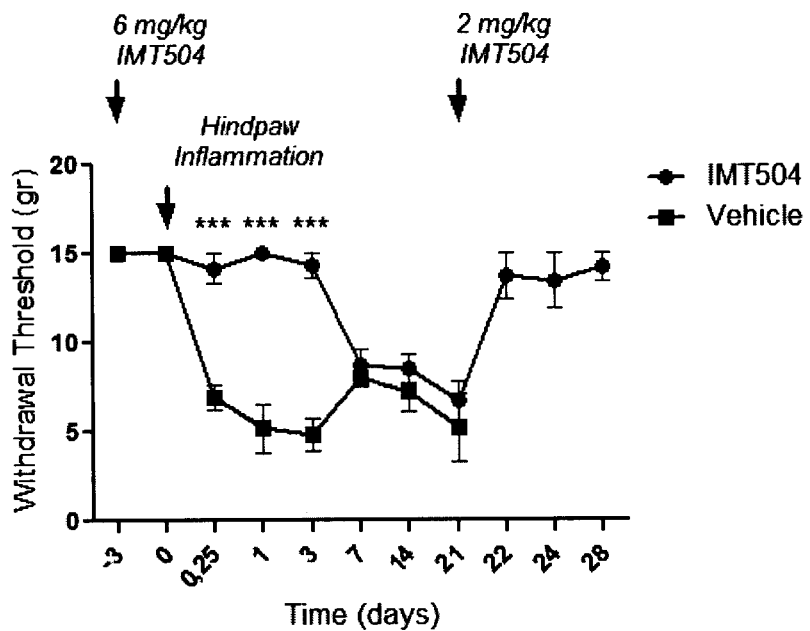
FIGS. 11A-11B show the effects of pre-emptive treatment with IMT504 (6 mg/kg; 72 h before injury) and a booster dose (2 mg/kg) by day 21 after injury, on mechanical and thermal allodynia in rats subjected to plantar inflammation: (A) Asterisks (*) show significant differences between ipsilateral hind paw withdrawal thresholds in rats treated with IMT504 vs. rats treated with vehicle. (B) Asterisks (*) show significant differences between the frequency of cold withdrawal (B) of hind paws in rats treated with IMT504 vs. rats treated with vehicle. A withdrawal threshold of less than 6 is considered allodynia.
Figure 11:
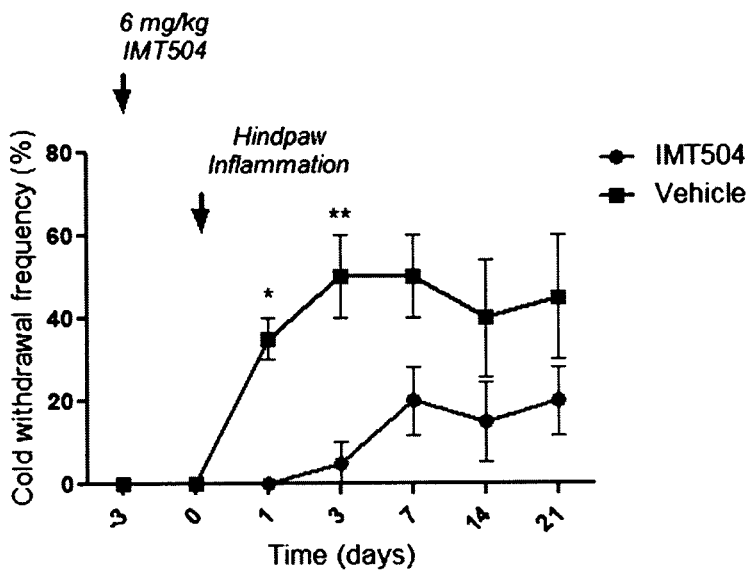

Effects of a Preventive Dose (6 mg/kg) and an Additional Booster Dose (2-3 Mg/Kg; 21 or 28 Days after Injury) of IMT504 on Mechanical Withdrawal Threshold and Cold Allodynia, in Rats with Chronic Inflammation An assay was conducted to address the preventive effect of IMT504 in rats with chronic inflammation. Two groups of four rats each were used. One group received a single dose of 6 mg/kg of IMT504 3 days before injury, with an additional booster dose of 3 mg/kg on day 28 after injury (FIG. 10). The second group received a single dose of 6 mg/kg of IMT504 3 days before injury, and a single additional administration of 2 mg/kg of IMT504, 21 days after injury (FIG. 11). Both groups received intra-plantar CFA, 3 days after the single dose of 6 mg/kg and their mechanical and thermal withdrawal thresholds were tested 1, 3, 7, 14, 21, 28, 29, and 35 days after injury (FIGS. 10 and 11). Additional groups of rats were prepared, that received intraplantar CFA and with (FIG. 11) or without (FIG. 10) preventive vehicle.

When compared to injured untreated or vehicle-treated rats, both groups receiving preventive treatment with IMT504 showed lack of mechanical allodynia until 3 (FIG. 10A) or 7 (FIG. 11A) days after injury. Mechanical withdrawal thresholds started a progressive decrease which was fully comparable to those of injured untreated or vehicle-treated rats by day 21 (FIG. 10A, 11A). A booster dose of IMT504, 28 (3 mg/kg; FIG. 10A) or 21 (2 mg/kg; FIG. 11A) days after injury completely restored the anti-allodynic effect of IMT504 (FIGS. 10A, 11A). This effect persisted during several days (FIG. 11A) before returning to allodynic levels (FIG. 10A).

Concerning responses to cold stimulation, rats receiving a single preventive dose of 6 mg/kg of IMT504, showed a slower progression towards cold allodynia which was significantly lower than that observed in injured vehicle-treated rats on days 1 and 3 after injury. Although differences were not statistically significant from day 7 on, rats treated with IMT504 always showed lower levels of cold allodynia than vehicle-treated rats (FIG. 11B).

Finally, both mechanical withdrawal thresholds as well as responses to cold stimuli in contralateral hind paws of all experimental animals remained normal during these assays (data not shown).

Effects of a Preventive Dose (6 mg/kg) of IMT504 on Dorsoventral Paw Thickness in Rats with Chronic Inflammation:

Injured rats receiving or not IMT504 showed consistently elevated hind paw dorsoventral thicknesses throughout the entire testing period, starting 1 day after injury (FIG. 10B). Preventive treatment with IMT504 did not seem to alter the natural course of hind paw inflammation, since the thickness was always elevated and comparable to that of untreated injured rats, from day 7 and onward (FIG. 10B). A comparison with naïve rats emphasized this effect even more.

Effects of Different Single Doses of IMT504 on Pain-Like Behavior in Rats with Hind Paw Inflammation.

Figure 12:
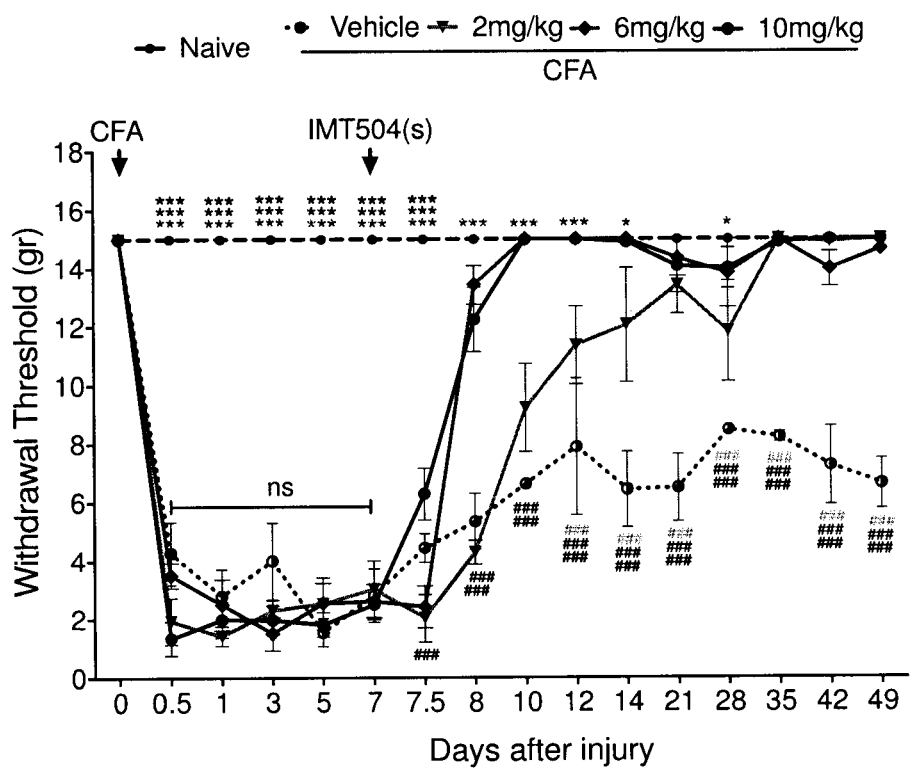
FIG. 12 shows the effects of late treatment using single doses of IMT504 on pain-like behavior in rats with hind paw inflammation: Time-line of CFA-induced hind paw inflammation. While naïve rats (n=5) virtually always exhibited basal withdrawal thresholds, all injured animal showed ipsilateral mechanical allodynia already 12 hours (h) after intraplantar CFA. Vehicle-treated CFA rats (n=4) remained allodynic throughout the whole tested period. Rats receiving a single dose of 6 mg/kg IMT504 (n=9) or 10 mg/kg IMT504 (n=9) remained allodynic only during the first week after injury, beginning recovery three days after initiation of the treatment, reaching basal ipsilateral withdrawal thresholds at day five after initiation of the treatment and onwards. Rats receiving 2 mg/kg IMT504 (n=9) showed a slower, incomplete recovery, never reaching basal withdrawal thresholds. Statistically significant differences between naïve vs. IMT504-treated (#) and rats treated with IMT504 vs. rats with CFA without treatment (vehicle) (*) are shown.

While naïve rats (n=5) virtually always exhibited basal withdrawal thresholds, all injured animal showed ipsilateral mechanical allodynia already 12 hours (h) after intraplantar CFA (a withdrawal threshold of less than 6 is considered as allodynia). Vehicle-treated CFA rats (n=4) remained allodynic throughout the whole tested period. In contrast, rats receiving a single dose of 6 mg/kg (n=9) or 10 mg/kg (n=9) of IMT504 were allodynic only during the first week after injury, before administration of IMT504, and began recovery 1 day after initiation of the treatment, reaching basal ipsilateral withdrawal thresholds 2-3 days later and onwards. Rats receiving a single dose of 2 mg/kg of IMT504 (n=9) showed a slower, but finally complete, recovery of basal withdrawal thresholds, from days 21 after injury and onwards. Statistically significant differences are shown between naïve and IMT504-treated rats (#) and CFA injured rats untreated and IMT504-treated (*) (see FIG. 12).

Effects of Treatment with a Single Dose of 6 mg/kg of IMT504 on Mechanical Thresholds in Rats in the Neuropathic Pain Model, Avoiding Nerve Injury.

Statistical analysis shows differences between contralateral hind paw withdrawal thresholds (unified in one single curve due to lack of differences between groups) and ipsilateral thresholds using numeral markers (#; black, contralateral vs. untreated SNI; red, contralateral vs. ipsilateral IMT504-treated) (a withdrawal threshold of less than 6 is considered as allodynia). Asterisks (*) show differences between ipsilateral hind paw withdrawal thresholds in SNI-untreated rats and the ipsilateral withdrawal thresholds in rats receiving IMT504 (see FIG. 4).

This invention is better illustrated in the following examples, which should not be construed as a limitation of its scope. On the contrary, it should be clearly understood that, after reading the present description other embodiments, modifications and equivalents may be possible, and envisioned by a person of skill in the art without departing from the spirit of the present invention and/or the scope of the appended claims.

EXAMPLES

Example 1

Experimental Animals:

Adult Sprague-Dawley male rats (200-300 g, BioFucal, Argentina) were kept in a twelve h light-cycle, with water and food ad libitum. All experiments performed were approved by the Institutional Animal Care and Use Committee (IACUC-IIMT; #17-02 and #17-04) of the IIMT, and were carried out according to the policy of the Society for Neuroscience and the International Association for the Study of Pain for use of animals in pain research.

Hind Paw Inflammation Model

In fifty-two rats anesthetized with Isoflurane (5% induction, 2.5% maintenance, 0.8 L/min O2 flow rate; Piramal Healthcare, UK), the right hind paw was injected intradermally with 100 µl of CFA (1:1, dissolved in normal saline; Sigma-Aldrich, Mo., USA), using a 1 ml syringe with a 25G needle attached. The animals (from now on, called CFA rats) were left to recover from anesthesia in a warm and quiet environment before relocating them in their corresponding cages.

Spared Nerve Injury Model (SNI)

In twenty-six rats anesthetized with Isoflurane (5% induction, 2.5% maintenance, 0.8 L/min O2 flow rate; Piramal Healthcare, UK), the right sciatic nerve and its three distal branches were exposed by blunt dissection, and the tibial and common peronneal branches completely sectioned and ligated to prevent regeneration. The third branch, the sural nerve, was left intact. The animals received one single injection of ketoprofen for post-surgical pain control and were left to recover from anesthesia in a warm and quiet environment before relocating them in their corresponding cages.

Experimental Drug

In all experiments, the ODN IMT504, with sequence 5'-TCATCATTTTGTCATTTTGTCATT-3') was used. The HPLC-grade phosphorothioate ODN (Oligos Etc. Inc., Integrated DNA Technologies, OR, USA) was suspended in sterile saline (0.9% NaCl; 20 mg/ml; storage concentration), and assayed for LPS contamination. For some experimental protocols the ODN was dissolved in saline solution to working concentrations (2 mg/ml (rats treated with 2 mg/kg)) or 0.2 mg/ml (rats treated with 0.2 mg/kg)), and administered at a final volume of 200-250 µl, depending on the animal weight.

Example 2: Treatment 1

Treatment Protocols Using IMT504 in Rats with Hind Paw Inflammation

In one set of experiments, called "preventive treatment", four rats received a daily dose of 20 mg/kg IMT504 for five consecutive days and four weeks later one dose of 6 mg/kg (group a); a second group of four rats received one dose of 6 mg/kg of IMT504 (group b) (FIG. 1A). Three days after the single injection of 6 mg/kg IMT504, all eight rats received intra-plantar CFA, after which they were tested for mechanical and cold allodynia during 21 days. At day 28, group b received an additional administration of IMT504 at a dose of 3 mg/kg and was evaluated until day 35.

In a second set of experiments, groups of rats were allocated to early or late treatment protocols (ET and LT, respectively), using a daily dose of 20 mg/kg IMT504 for five consecutive days (FIG. 2A). The ET protocol (n=5) was performed immediately after the intradermal injection of CFA in the hind paw; the LT protocol (n=5) was initiated seven days after the induction of hind paw inflammation (FIG. 2A). In all cases, animals where tested for pain-like behavior during four weeks after the induction of hind paw inflammation (days 1, 3, 7; weeks 2, 3 and 4).

In a third set of experiments, different concentrations and dosages of IMT504 were administered subcutaneously using the LT protocol (FIG. 3A). Rats were separated in three groups (n=5 per group) and treated as follows: i) a daily dose of 0.2 mg/kg of IMT504 for five consecutive days, ii) a daily dose of 2 mg/kg of IMT504 for five consecutive days, and iii) a daily dose of 2 mg/kg of IMT504 for three consecutive days. All these groups were tested for pain-like behavior up to seven weeks after induction of the hind paw inflammation.

Treatment Protocols Using IMT504 in Rats with SNI

Rats were administered subcutaneously using the LT protocol (FIG. 4A) and a single dose of 6 mg/kg of IMT504. This was followed by pain-like behavior testing for up to six weeks after SNI.

Control Groups

Naïve (uninjured and untreated; n=16), CFA injured untreated (n=10), and vehicle-treated CFA (n=9) or SNI rats (n=10) were used as controls. Eight naïve rats remained untreated, four were vehicle-treated, and four received a daily dose of 20 mg/kg IMT504 for five consecutive days. Untreated CFA rats received an intradermal hind paw injection of CFA and no further treatment. Vehicle-treated CFA rats received five daily subcutaneous injections of saline (200 µl), starting seven days after injury. Vehicle-treated SNI rats received one single dose of saline (200 ul), starting seven days after injury.

Behavioral Assessment

Behavioral assessment was performed during daytime in all animals before any intervention (basal responses) and at different time-points after injury and IMT504 or vehicle administration.

For mechanical allodynia assessment, a set of von Frey filaments (Stoelting, Ill., USA) and the modified up-down method of Dixon were used, as described by Chaplan et al. (Chaplan S R, et, al., (1994) *J. Neurosci Methods* 53: 55-632) to establish the 50% withdrawal threshold. A withdrawal threshold of 6 g or less was considered an allodynic response.

For acute thermal nociception assessment, the tail immersion test was used. The latency of tail-flick reflex to swift immersion of the last 3 cm of the tip of the tail of each rat on a hot bath (52° C.) was measured using a stopwatch (resolution of 0.01 s). This was repeated three times, with 10 s intervals, and an average response was obtained.

For cold allodynia assessment, the reaction to the application of a drop of acetone onto the plantar surface of the hind paw was used. Both frequency of withdrawal and cold score (pain-like behavior intensity) were measured.

Statistical Analysis

All data was expressed as mean±S.E.M and evaluated using GraphPad Prism 7.0a (all data underwent standard normality analysis). Behavioral data was statistically analyzed using two-way repeated measures analysis of variance (two-way ANOVA), followed by the Bonferroni post-hoc test. P values are presented as follows: ns, $p>0.05$; $*0.05>p>0.01$; $0.01>p>0.001$, $*p<0.001$ and $****p<0.0001$.

Example 3: Treatment 2

Post-Incisional Pain Model

In twenty-four rats anesthetized with Isoflurane (5% induction, 2.5% maintenance, 0.8 L/min 02 flow rate; Scott-Cassará, Argentina), the right hind paw plantar skin was cleaned and disinfected. This was followed by a 1-cm longitudinal incision distal to heel and extending towards the toes, as previously described (Xu J, et al., 2011, 24(5): 508-514). The incision involved both plantar skin and fascia. This was followed by identification and longitudinal incision of plantar extensor muscle, leaving its insertions intact. After achieving homeostdsica, skin was sutured using a 5-0 nylon suture, protected with an antibacterial cream and the animal was returned to its retention cage, under observation, until full recovery from anesthesia.

Hind Paw Inflammation Model

In seventeen rats anesthetized with Isoflurane (5% induction, 2.5% maintenance, 0.8 L/min 02 flow rate; Scott-Cassará, Argentina), the right hind paw was injected intradermally with 100 µl of CFA (1:1, dissolved in normal saline; Sigma-Aldrich, Mo., USA), using a 1 ml syringe with a 25G needle. The animals (called CFA rats) were left to recover from anesthesia in a warm and quiet environment before relocating in their corresponding cages.

Treatment Protocols with IMT504 in Rats with Post-Incisional Pain

Rats were subcutaneously administered 6 mg/kg of IMT504, 48 and 24 h before implementing the post-incisional pain model. This was followed by pain-like behavior testing for up to 21 days after injury.

Treatment Protocols Using IMT504 in Rats with Hind Paw Inflammation

Figure 2:
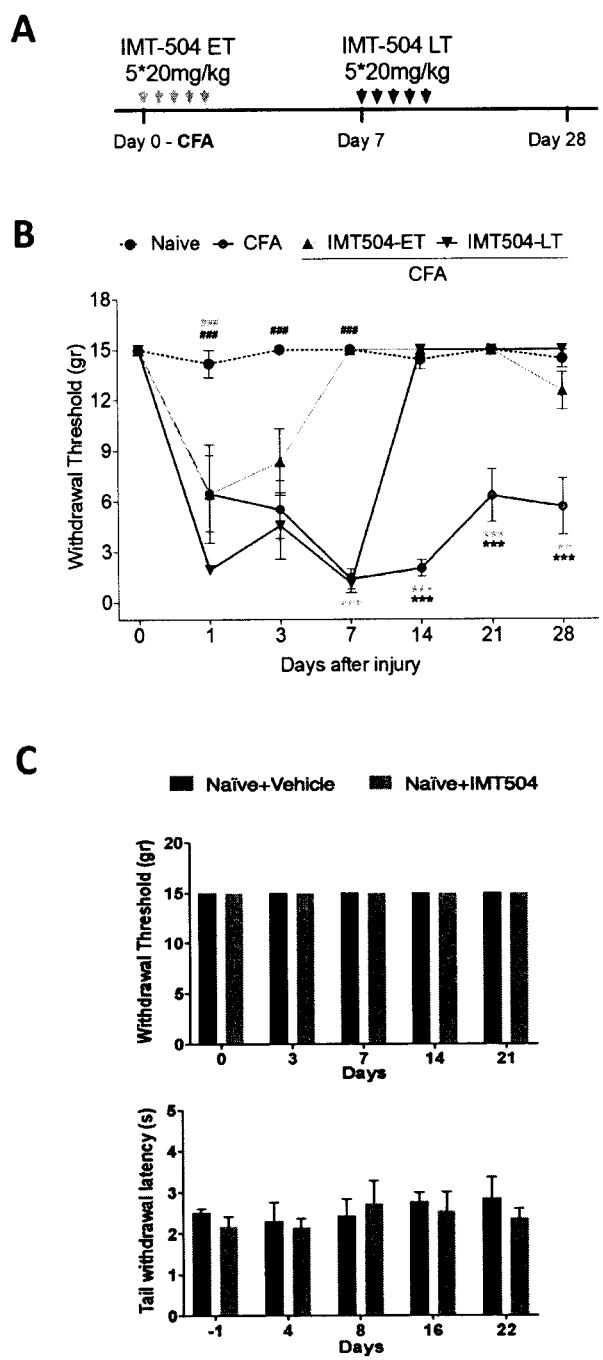
FIGS. 2A-2C show the effects of early treatment (ET) and late treatment (LT) of high doses of IMT504 on pain-like behavior in rats with hind paw inflammation.

Eight rats received a dose of 6 mg/kg IMT504 (FIGS. 2 and 3). Three days after the single injection of 6 mg/kg IMT504, all rats received intra-plantar complete Freund's Adjuvant (CFA), after which they were tested for mechanical and cold allodynia during 21-35 days. On day 28 (FIG. 1) or 28 (FIG. 2), rats receiving preventive IMT504 were administered additional IMT504 at a dose of 3 mg/kg (FIG. 1) or 2 mg/kg (FIG. 2), and assessed until days 21-35.

Control Groups

Naïve rats (non-injured and untreated; n=4), untreated CFA-injured rats (n=5) and vehicle-treated CFA rats (n=4) were used as controls. Untreated CFA rats received an intradermal hind paw injection of CFA and no further treatment. Vehicle-treated CFA rats received a subcutaneous injection of saline solution (200 µl).

Behavioral Assessment

Behavioral assessment was performed during daytime in all animals before any intervention (basal responses) and at different time-points after injury and IMT504 or vehicle administration.

For mechanical allodynia assessment, a set of von Frey filaments (Stoelting, Ill., USA) and the modified up-down method of Dixon were used, to establish the 50% withdrawal threshold. A withdrawal threshold of 0.21 oz or less was considered an allodynic response.

For cold allodynia assessment, the reaction to the application of a drop of acetone onto the plantar surface of the hind paw was used, as previously described. Frequency of withdrawal to cold stimuli was measured.

The invention claimed is:

1. A method for preventing post-surgical neuropathic and/or inflammatory pain, wherein the method comprises administering at least one effective dose of the phosphorothioate oligonucleotide IMT504 to a human prior to a surgical procedure, wherein the oligonucleotide IMT504 has the nucleotide sequence set forth in SEQ ID NO. 1.

2. The method according to claim 1, wherein;
at least one dose from 6 mg/kg to 20 mg/kg is applied in a time period between 24 hours and 5 days prior to onset of surgery.

3. The method according to claim 1, comprising the administration of two doses of 6 mg/kg, 48 and 24 hours prior to the surgery.

4. The method according to claim 1, wherein the administration is selected from the group consisting of intravenous, intramuscular, subcutaneous, epidural, and intrathecal.

\* \* \* \* \*